United States Patent [19]
Ikeda

[11] 4,397,747
[45] Aug. 9, 1983

[54] APPARATUS FOR PLASMA SEPARATION/EXCHANGE BY DOUBLE FILTRATION

[75] Inventor: Saburo Ikeda, Saiki, Japan

[73] Assignees: Kawasumi Laboratories, Inc., Tokyo; Kuraray Co., Ltd., Kurashiki, both of Japan

[21] Appl. No.: 283,227

[22] Filed: Jul. 14, 1981

[30] Foreign Application Priority Data

Jul. 18, 1980 [JP] Japan .................... 55-98236

[51] Int. Cl.³ .................. B01D 13/00; B01D 31/00
[52] U.S. Cl. .................. 210/641; 210/651;
210/744; 210/86; 210/104; 210/105; 210/110;
210/111; 210/116; 210/134; 210/137; 210/203;
210/257.2; 210/259; 210/321.1; 210/335;
210/433.2
[58] Field of Search .......... 210/637, 641, 86, 644–651,
210/87, 741, 744, 806, 101, 104, 105, 110, 111,
116, 134, 137, 201, 202, 203, 257.2, 259, 295,
321, 335, 433, 927, 90, 436

[56] References Cited
U.S. PATENT DOCUMENTS

| 3,579,441 | 5/1971 | Brown | 210/641 X |
| 3,619,423 | 11/1971 | Galletti et al. | 210/641 X |
| 3,844,171 | 10/1974 | Rodger | 73/293 |
| 3,854,907 | 12/1974 | Rising | 210/436 X |
| 3,946,731 | 3/1976 | Lichtenstein | 210/87 X |
| 4,248,087 | 2/1981 | Dennis et al. | 73/290 V |

FOREIGN PATENT DOCUMENTS 55-2444 1/1980 Japan ................ 210/321.2

OTHER PUBLICATIONS

Malchesky, P. S. et al. "On-Line Separation of Macromolecules . . .," Artificial Organs, vol. 4, No. 3, Aug. 1980, pp. 205–207.
Agishi et al., Japanese Journal of Medical Instrumentation, vol. 49, Supplement, pp. 259–261, 1979.

Primary Examiner—David R. Sadowski
Attorney, Agent, or Firm—Barry Kramer

[57] ABSTRACT

The invention provides an apparatus for plasma separation/exchange by double-step-membrane filtration, namely separation of blood into plasma and a corpuscular fraction and separation of high-molecular-weight substances (e.g. gamma-globulin) in the plasma from low-molecular-weight substances (e.g. albumin), and addition of a substitute fluid. A method of treating blood is also provided.

The apparatus and method are effective e.g. in the treatment of blood of patients with peripheral circulatory insufficiency due to arteriosclerosis and of patients with rheumatoid arthritis, which is an autoimmune disease.

5 Claims, 5 Drawing Figures

APPARATUS FOR PLASMA SEPARATION/EXCHANGE BY DOUBLE FILTRATION

BACKGROUND OF THE INVENTION

1. Field of the Invention

This invention relates to an apparatus for conducting plasma separation/exchange by double filtration in a safe and steady manner.

2. Description of the Prior Art

Plasma separation and exchange is a recently developed therapy for renal failure, hepatic failure, autoimmune diseases and so on. This technique, like blood dialysis, generally comprises separating plasma continuously in a closed extracorporeal circuit and returning a plasma fraction to the body of the patient. Another plasma fraction, which is discarded, contains low-molecular-weight active components bound to high-molecular-weight toxins or the like, and removal of these necessitates a correspondingly larger amount of substitute fluid. Therefore, various attempts have so far been made to remove such high-molecular-weight substances in an efficient manner. Among others, plasma separation and exchange is noteworthy. This technique uses two filter means which are different in their low-molecular-weight substance cut-off performance. The first filter means performs separation into a plasma fraction and a corpuscular fraction, and the second filter means separates the plasma fraction into a high-molecular-weight fraction and a low-molecular-weight fraction. The high-molecular-weight fraction alone is selectively removed and the low-molecular-weight-fraction is returned to the body.

Pioneer studies of the specific plasma component permeation method have already been made and described. For example, there is a report by T. Agishi et al, published in the *Japanese Journal of Medical Instrumentation*, vol. 49, Supplement, p. 259–261 (1979). Also, a Japanese patent application laid open under No. 2444/1980 discloses a blood treatment apparatus in which a specific plasma component permeation method is realized in combination with a water-removing means.

However, these techniques known in the art, though called techniques, are no more than proposals of possibilities or theoretical apparatus. No disclosure is contained therein for an actual apparatus useful in medical practice.

SUMMARY OF THE INVENTION

This invention provides an apparatus which enables plasma separation/exchange by double filtration in a safe and steady manner by systematizing such a technique so that the pressure and flow rate within the closed extracorporeal circuit can be controlled automatically.

DETAILED DESCRIPTION OF THE INVENTION

Figure 1:
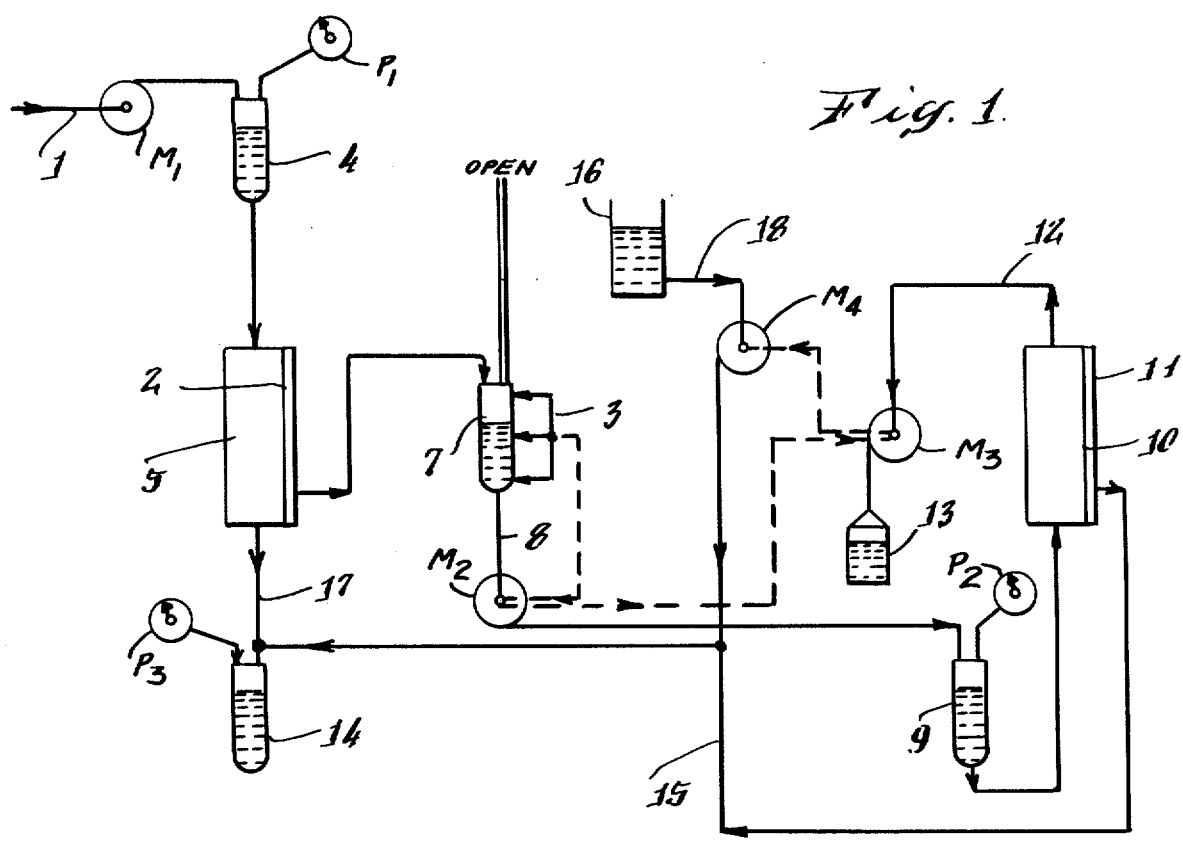
FIG. 1 is a schematic representation of one embodiment of the apparatus of the invention.

In accordance with the present invention, separation of blood into plasma and corpuscular components and separation of the plasma into a high-molecular-weight and a low-molecular-weight fraction are carried out using two membrane modules of different kinds. One of these modules is called a plasma separation membrane module ("first membrane module" or "first filter") and the other is called a plasma fraction fractionation membrane module ("second membrane module" or "second filter"). The membrane to be used in the first membrane module (first filter), i.e., to be used for separating corpuscular components from plasma, is a microporous membrane having an average effective pore size of 0.02–0.4 micron, preferably about 0.1 micron. Preferably, this membrane will be a homogeneous microporous membrane, a microfiltration membrane or a so-called asymmetrical membrane comprising a porous supporting layer and a relatively dense microporous layer. Pore sizes larger than 0.4 micron often lead to hemolysis, whereas pore sizes smaller than 0.02 micron cut off such proteins as gamma-globulin, and therefore cannot be used to give a plasma containing these proteins. Examples of such membrane are substantially uniform microporous membranes made of polyvinyl alcohol (PVA) type polymers, separately developed by one of the present inventors, as well as other substantially uniform microporous membranes and asymmetrical membranes made of ethylene-vinyl alcohol (EVA) copolymers, cellulose derivatives (e.g. cellulose acetates), polyolefins, polyacrylonitriles, polyamides, polyesters, polysulfones, and so on. Preferred among these are PVA, EVA, cellulose derivative and polysulfone membranes, which have good biocompatibility.

The membrane used in the second membrane module (second filter) separates plasma into a high-molecular-weight fraction and a low-molecular-weight fraction. The boundary molecular weight can optionally be set depending on the desired purpose. The apparatus of the present invention can be used in the treatment of autoimmune diseases and thus, in one embodiment, the molecular-weight cut-off boundary can be set at 100,000. Pathogenic substances in autoimmune diseases are often present in the form bound to gamma-globulin having a molecular weight of about 160,000. Therefore, it is desirable that substances having molecular weights of about 160,000 and higher be removed but substances having lower molecular weights such as albumin (molecular weight=67,000) useful to the organism be returned. Thus, setting the boundary molecular weight at 100,000 can result in rigid separation of the above-mentioned gamma-globulin and albumin. The boundary of molecular-weight cut-off should be selected depending on the molecular weight of the pathogenic substance to be removed, and in another case where an immune complex is the causative factor, it is set at 100,000–200,000.

As the second membrane, there can be used any membrane that can fractionate plasma under pressure. In this sense, membranes having ultrafiltration capacity can widely be used. No special limitations are placed on the membrane structure, and the above-mentioned uniform microporous membranes, asymmetrical membranes and uniform gel membranes can be used. The term "uniform gel membranes" as used herein means membranes having substantially no micropores or tiny gap structures among joined particles when observed in the dry or wet state under an electron microscope at a magnification of 24,000.

The membranes mentioned above are used in the form of flat membranes or hollow fiber membranes and constitute membrane modules. In view of the simplicity of module preparation and the possibility of miniaturization, hollow fiber membranes are preferred.

FIG. 1 shows an embodiment of the present invention. The construction and working thereof are described simultaneously.

In the drawings, (3) is a plasma level sensor, (5) is a first filter, (7) is a plasma reservoir, (8) is a plasma outlet circuit, (11) is a second filter, (12) is a high-molecular-weight fraction outlet circuit, (15) is a low-molecular-weight fraction outlet circuit, (18) is a substitute fluid inlet circuit, ($M_1$), ($M_2$), ($M_3$) and ($M_4$) are pumps and ($P_1$), ($P_2$) and ($P_3$) are pressure gauges.

First, the blood is withdrawn from a patient and introduced into the apparatus through a blood inlet by means of pump ($M_1$), and retained in blood reservoir (4) for a while. Said blood reservoir is equipped with pressure gauge $P_1$ for monitoring the reservoir for abnormal hypertension e.g. due to clogging of first filter (5) which is connected with the reservoir. The blood flow rate through pump ($M_1$) is adjusted to 100 ml/minute to 200 ml/minute, preferably 100 ml/minute to 150 ml/minute. The pressure on $P_1$ is maintained at 80 mmHg to 150 mmHg, preferably 80 mmHg to 120 mmHg.

This first filter (5) is partitioned with filter membrane (2), e.g. a polyvinyl alcohol hollow fiber membrane having a substantially uniform microporous structure with an average pore size of 0.04 micron, an inside diameter of 400 microns and membrane thickness of 200 microns. The blood introduced from blood reservoir (4) into said filter is separated into a corpuscular fraction and a plasma fraction by means of said filter membrane (2) under influence of a negative pressure produced by pump ($M_2$) provided in plasma outlet circuit (8). The plasma fraction separated therein is sent to a second filter (11) through plasma reservoirs (7) and (9) provided in plasma outlet circuit (8). On that occasion, if the pressure of the plasma separated should be outside specified limits (e.g. in the case of an abnormal negative pressure being produced), there would arise a risk of hemolysis, for instance.

Therefore, plasma reservoir (7) is provided in plasma outlet circuit (8) which connects first filter (5) with second filter (11). The plasma level in said plasma reservoir (7) is monitored by liquid level sensor (3), and the rotation frequency of pump ($M_2$) is automatically modified or switched on or off by controlling this sensor (3) and in association with each other, so that the flow rate can be adjusted so as to maintain the plasma level within specified limits. According to this control, abnormal negative pressure in plasma reservoir (7) is surely avoided, and a risk of hemolysis is therefore also avoided. Thus, for example, when the plasma level falls below a specified limit, the rotation frequency of pump ($M_2$) can adequately be reduced or the pump can be stopped for a while.

It is preferable that plasma reservoir (7) be open to the atmosphere, and the opening part should preferably be provided with a sterilizing filter. By keeping the plasma reservoir open to the atmosphere, the pressure therein is always kept at atmospheric pressure.

Figure 3:
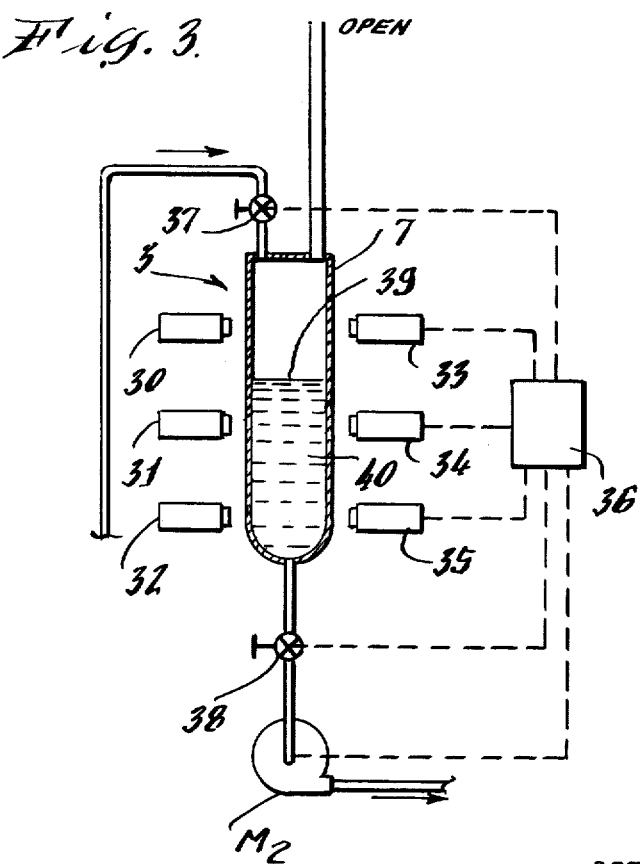
FIGS. 3, 4 and 5 are schematic representations of plasma level sensing systems for use in conjunction with the plasma reservoir of the apparatus of the invention.
Figure 4:
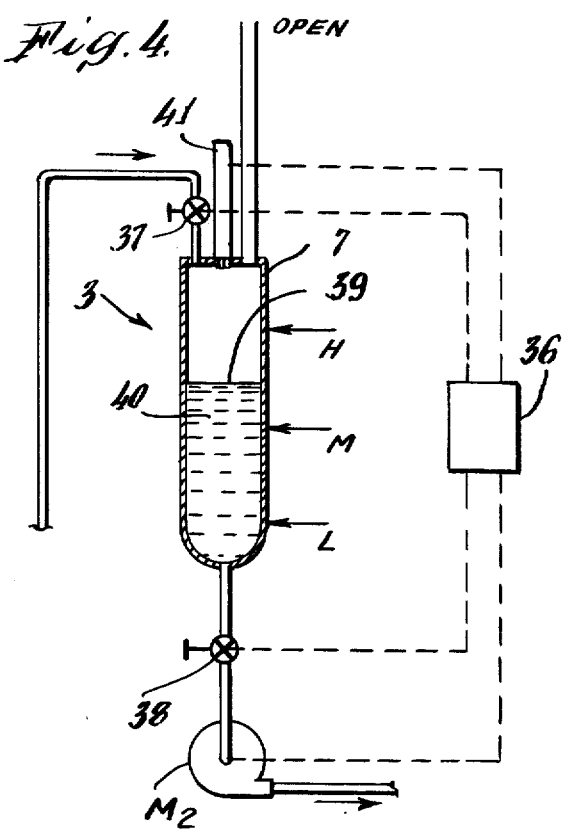
Figure 5:
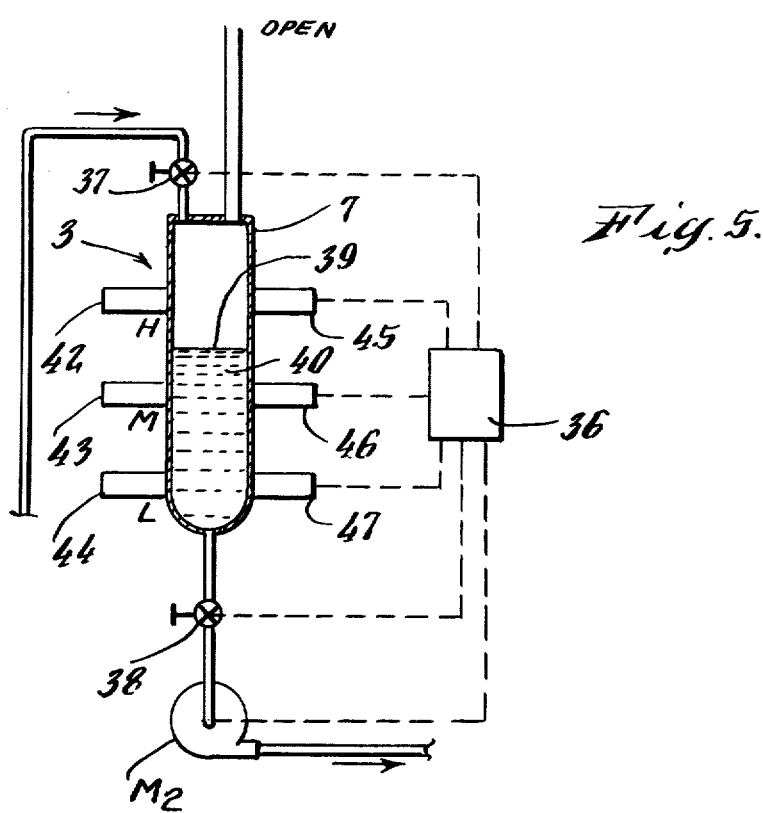

Each of FIGS. 3, 4 and 5 shows a schematic representation of an example of a plasma reservoir (7) and a plasma level sensor (3) in accordance with the present invention.

In FIG. 3, a photoelectric cell type plasma level sensor, comprising light emitters (30), (31) and (32) along with light acceptors (33), (34) and (35), is provided with the light emitters and light acceptors on opposite sides of plasma reservoir (7). The light emitters and acceptors are arranged in three sections, namely, an upper part ("H"), a middle part ("M") and a lower part ("L"). A pump ($M_2$) and pinch valves (37) and (38) are controlled in association with light acceptors (33), (34) and (35) through control system (36). According to an association of pinch valves (37) and (38) with light acceptors (33), (34) and (35), safer operation can be conducted. However, in this invention, an association of pinch valves with light acceptors is not essential.

When the level (39) of plasma (40) in a plasma reservoir (7) is above the H level, pinch valve (37) is controlled in association with light acceptors (33), (34) and (35) through control system (36), and is closed. When the plasma level (39) falls below level H, pinch valve (37) is opened again. When the plasma level (39) is between level H and level M, pump $M_2$ is controlled in association with light acceptors (33), (34) and (35) through control system (36), to maintain the rotation frequency of pump ($M_2$) relatively high. When the plasma level (39) falls to a level between level M and level L, pump ($M_2$) is controlled in association with light acceptors (33), (34) and (35) through control system (36) to reduce the rotation frequency of pump ($M_2$). When the plasma level (39) falls below level L, pinch valve (38) and pump ($M_2$) are controlled in association with light acceptors (33), (34) and (35) through control system (36) to close pinch valve (38) and stop pump $M_2$. When the plasma level (39) subsequently rises above level L, pinch valve (38) is opened and pump $M_2$ is turned back on.

In FIG. 4, ultrasonic wave apparatus 41 (which comprises a combination of an ultrasonic wave generator and an ultrasonic wave acceptor) is provided on the upper part of plasma reservoir (7). By directing ultrasonic waves to the top surface of plasma 40 at level 39 at regular intervals and detecting the reflecting waves, the position of plasma level 39 can be measured.

Pump ($M_2$) and pinch valves (37) and (38) are controlled in association with ultrasonic wave apparatus 41 through control system (36). The operation is essentially the same as described above in conjunction with FIG. 3.

In FIG. 5 ultrasonic wave generators (42), (43) and (44) and ultrasonic wave acceptors (45), (46) and (47) are provided on opposite sides of plasma reservoir (7). Respective pairs of ultrasonic wave generators and acceptors cover plasma levels H, M and L. Again the operation of this embodiment is essentially the same as that of the embodiment shown in FIG. 3.

Among the above three systems of FIGS. 3, 4 and 5, the system of FIG. 3 is the most practical and effective.

The inside of second filter (11) mentioned above and shown in FIG. 1 is partitioned with filter membrane (10), e.g. an ethylenevinyl alcohol copolymer membrane having an asymmetrical structure comprising a porous support layer and a microporous layer with an average micropore size of 110 Angstroms, an inside diameter of 330 microns and a membrane thickness of 45 microns as disclosed in the Japanese Patent Application Kokai (laid open) No. 35969/1980. The plasma introduced into said second filter (11) is separated into a high-molecular-weight fraction and a low-molecular-weight fraction under influence of a positive pressure produced by the flow rate difference between pump ($M_2$) mentioned above and pump ($M_3$) provided in outlet circuit (12). The high-molecular-weight fraction thus separated is withdrawn through outlet circuit (12) into reservoir (13). If the rates of flow through pump ($M_2$) and pump ($M_3$) are unbalanced, an abnormal pressure is exerted on second filter (10), whereby steady and stable filtration is inhibited.

Therefore, in accordance with the present invention, the flow rate ratio between pump ($M_2$) and pump ($M_3$) is controlled so that the flow rate ratio between the plasma introduced into second filter (11) and the high-molecular-weight fraction withdrawn from said second filter can be maintained at a predetermined value. According to this control, a change in fractionation performance of the second filter is positively avoided. For example, when the rate of flow through pump ($M_2$) is 12-45 ml/minute, the rate of flow through pump ($M_3$) is automatically adjusted to ⅓ to ¼ of the former, namely to 3-15 ml/minute. In FIG. 1, ($P_2$) is a pressure gauge provided for monitoring plasma reservoir (9), necessary because there is a risk of filter membrane (10), for instance, being ruptured when second filter (11) is exposed to high pressure. The pressure on $P_2$ is maintained at 200 mmHg to 300 mmHg, preferably 230 mmHg to 270 mmHg.

The low-molecular-weight fraction separated in second filter (11) mentioned above is sent to blood reservoir (14) through outlet circuit (15). This fraction is combined with the corpuscular fraction coming from first filter (5) through outlet circuit (17), and returned to the body of the patient. To supplement the plasma fraction removed in second filter (11), albumin, hydroxy ethyl starch (HES) or other substitute fluid is supplied from substitute fluid container (16) to blood reservoir (14) through inlet circuit (18). In accordance with the invention, the flow rate of such substitute fluid, which is introduced, is adjusted through associated control of pump ($M_4$) for substitute fluid introduction disposed in inlet circuit (18) and pump ($M_3$) disposed in high-molecular-weight fraction outlet circuit (12) so that the amount of the high-molecular-weight fraction withdrawn and the amount of the substitute fluid introduced are equal. For example, when the flow rate through pump ($M_3$) is, as above mentioned, 3-15 ml/minute, then pump ($M_4$) is adjusted so that the flow rate therethrough be equal to that rate, whereby the substitute fluid can be poured into blood reservoir (14) without excess or deficiency. Furthermore, in this embodiment, blood reservoir (14) is provided with pressure gauge ($P_3$) for monitoring the condition of the patient (e.g. anemia) and possible troubles in the shunt. The pressure on $P_3$ is maintained at 80 mmHg to 150 mmHg, preferably 80 mmHg to 120 mmHg.

Figure 2:
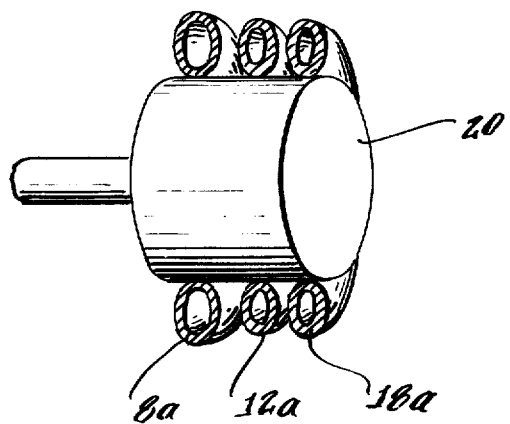
FIG. 2 is a schematic representation of a flow rate control useful in the operation of the apparatus of the invention.

In accordance with this invention, associated control of pumps ($M_2$), ($M_3$) and ($M_4$) may be carried out electrically. Alternatively, as shown in FIG. 2, such flow rate control can be made by pressing in a squeezing manner tube (8a) in circuit (8) and tubes (12a) and (18a) in circuits (12) and (18). The tubes have different inside diameters [e.g. inside diameter of tube (8a) being 8 mm and inside diameter of tubes (12a), (18a) being 4 mm] and are simultaneously squeezed to control the flow rate therethrough with a single driving roller (20). In this case, flow rate control corresponding to the tube diameters is possible.

The foregoing is a description of a preferred embodiment of the invention. First filter (5) and second filter (11) may be of the hollow fiber type or of any other type. Other elements may also be modified in accordance with the gist of the invention.

According to this invention, it is now possible to conduct very safe and steady treatment, since, in plasma separation by double filtration, the flow rate and pressure within the closed extracorporeal circuit provided with a first filter and a second filter are automatically controlled and consistently maintained at respective specified values. The practical results obtained through the use of the invention are excellent.

The treatment system of the present invention can effectively be used in the treatment of the blood of patients with the following disorders, autoimmune hemolytic anemia, idiopathic thrombocytopenic purpura, chronic glomerulonephritis, Goodpasture syndrome, systemic lupus erythematosus, progressive systemic schlerosis, etc.

What is claimed is:

1. An apparatus for plasma separation and exchange utilizing double filtration comprising:
   a first filter means for separating the blood withdrawn from a patient's body into a corpuscular fraction and a plasma fraction;
   a second filter means for receiving the plasma fraction from said first filter means for separating said plasma fraction further into a high-molecular-weight fraction and a low-molecular-weight fraction containing albumin;
   means to combine said corpuscular fraction from said first filter means with said low-molecular-weight fraction from said second filter means;
   means for adding an additional fluid to the combined corpuscular and low-molecular-weight fractions;
   a plasma reservoir between said first and second filter means for receiving said plasma fraction from said first filter means on its way to said second filter means, said reservoir having an opening which is vented to the atmosphere;
   level sensing means for monitoring the plasma level within said plasma reservoir;
   a first pump means controlled in association with said level sensing means for adjusting the flow rate of plasma between said first and second filter means for maintaining the plasma level in said reservoir within a predetermined range;
   a second pump means for controlling, in association with said first pump means, the flow rate of said high-molecular-weight fraction exiting from said second filter means for maintaining the flow rate ratio between the plasma entering said second filter means and the high-molecular-weight fraction withdrawn therefrom at a predetermined value; and
   a third pump means for controlling, in association with said second pump means, the flow rate of additional fluid provided by said adding means so that the amount of high-molecular-weight fraction withdrawn from said second filter means is equal to the amount of additional fluid added by said adding means.

2. The apparatus of claim 1 further comprising a sterilizing filter attached to the opening in the plasma reservoir.

3. The apparatus of claim 1 wherein said level sensing means comprises ultrasonic wave transmitting and receiving means.

4. The apparatus of claim 1 wherein said level sensing means comprises light emitting and light sensing means.

5. A method for separating and exchanging blood plasma comprising:

separating the blood withdrawn from a patient's body into a corpuscular fraction and a plasma fraction in a first filter;

passing said plasma fraction through a plasma reservoir, vented to the atmosphere, on its way to a second filter;

separating said plasma fraction further into a high-molecular-weight fraction and an albumin-containing low-molecular-weight fraction in said second filter;

combining said corpuscular fraction from said first filter with said low-molecular-weight fraction from said second filter;

adding an additional fluid to the combined corpuscular and low-molecular-weight fractions in an amount equal to the amount of high-molecular-weight fraction separated from said plasma fraction in said second filter;

monitoring the plasma level within said plasma reservoir;

maintaining said plasma level within a predetermined range by adjusting the flow rate of plasma between said first and second filters in response to the monitored level of plasma within said plasma reservoir; and maintaining the flow rate ratio between the plasma entering said second filter and the high-molecular-weight fraction withdrawn therefrom at a predetermined value by controlling the flow rate of the high-molecular-weight fraction exiting from said second filter.

* * * * *